United States Patent
Pace et al.

(10) Patent No.: US 6,263,875 B1
(45) Date of Patent: Jul. 24, 2001

(54) CHILD NASAL DECONGESTING DEVICE

(76) Inventors: Teata Pace; Emory Pace, both of 25027 Hwy. #365, North Little Rock, AR (US) 72113

( * ) Notice: Subject to any disclaimer, the term of this patent is extended or adjusted under 35 U.S.C. 154(b) by 0 days.

(21) Appl. No.: 09/311,418

(22) Filed: May 13, 1999

(51) Int. Cl.⁷ .................................................. A61M 15/08
(52) U.S. Cl. ................................ 128/207.18; 128/200.22
(58) Field of Search ........................ 128/207.18, 207.16, 128/207.12, 201.25, 201.26, 201.28, 202.15, 206.21, 206.22, 206.28, 200.22, 203.22, 203.28, 204.28, 205.13, 206.29; 604/37, 36, 212, 187, 215, 313, 316; 606/162, 196

(56) References Cited

U.S. PATENT DOCUMENTS

| | | | |
|---|---|---|---|
| 258,632 | * | 5/1882 | Cooper et al. ................. 128/203.28 |
| 297,427 | * | 4/1884 | McGregor ...................... 128/203.28 |
| 1,848,232 | * | 3/1932 | Swope et al. .................. 128/205.23 |
| 2,292,568 | * | 8/1942 | Kanter et al. ........................ 128/198 |
| 2,560,746 | * | 7/1951 | Scarkino .............................. 128/232 |
| 2,612,894 | * | 10/1952 | Akins .................................. 128/250 |
| 2,655,918 | * | 10/1953 | Jones ............................... 128/200.22 |
| 2,763,263 | * | 7/1956 | Ellman ............................ 128/203.28 |
| 3,599,634 | * | 8/1971 | Englesson ......................... 128/145.7 |
| 3,683,908 | * | 8/1972 | Michael et al. ................. 128/205.23 |
| 4,566,451 | * | 1/1986 | Badewien ........................ 128/200.21 |
| 4,706,683 | * | 11/1987 | Chilton et al. ....................... 128/654 |
| 4,945,918 | * | 8/1990 | Abernathy .............................. 128/719 |
| 5,290,257 | * | 3/1994 | Zhong ................................. 604/212 |
| 5,398,676 | * | 3/1995 | Press et al. ..................... 128/204.23 |
| 5,496,268 | * | 3/1996 | Perla ..................................... 604/27 |

FOREIGN PATENT DOCUMENTS

| | | | |
|---|---|---|---|
| 118133 | * | 2/1943 | (AU) .............................. 128/200.22 |
| 642872 | * | 3/1937 | (DE) .............................. 128/200.22 |

* cited by examiner

Primary Examiner—Aaron J. Lewis
Assistant Examiner—Teena Mitchell

(57) ABSTRACT

A child nasal decongesting device for relieving nasal congestion in children. The child nasal decongesting device includes a bulb defining an air cavity therein and a facemask outwardly extending from the bulb. The facemask has an open distal end opposite the bulb designed for positioning over a mouth and nostrils of a user such that the mouth and nostrils of the user are covered by the distal end of the facemask. An elongate tube outwardly extends from the bulb through the facemask. The tube is in fluid communication with the air cavity and has an open distal end outwardly extending from the distal end of the facemask and which is designed for insertion into the mouth of the user when the distal end of the facemask is positioned over the user's mouth and nostrils.

9 Claims, 2 Drawing Sheets

CHILD NASAL DECONGESTING DEVICE

BACKGROUND OF THE INVENTION

1. Field of the Invention

The present invention relates to nasal decongesting devices and more particularly pertains to a new child nasal decongesting device for relieving nasal congestion in children.

2. Description of the Prior Art

The use of nasal decongesting devices is known in the prior art. More specifically, nasal decongesting devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5752,510; U.S. Pat. No. 2,501,279; U.S. Pat. No. 2,946,332; U.S. Pat. No. 4,817,626; U.S. Pat. No. 3,949,751; and U.S. Pat. No. Des. 299,866.

While these devices fulfill their respective, particular objectives and requirements, the aforementioned patents do not disclose a new child nasal decongesting device. The inventive device includes a bulb defining an air cavity therein and a facemask outwardly extending from the bulb. The facemask has an open distal end opposite the bulb designed for positioning over a mouth and nostrils of a user such that the mouth and nostrils of the user are covered by the distal end of the facemask. An elongate tube outwardly extends from the bulb through the facemask. The tube is in fluid communication with the air cavity and has an open distal end outwardly extending from the distal end of the facemask and which is designed for insertion into the mouth of the user when the distal end of the facemask is positioned over the user's mouth and nostrils.

In these respects, the child nasal decongesting device according to the present invention substantially departs from the conventional concepts and designs of the prior art, and in so doing provides an apparatus primarily developed for the purpose of relieving nasal congestion in children.

SUMMARY OF THE INVENTION

In view of the foregoing disadvantages inherent in the known types of nasal decongesting devices now present in the prior art, the present invention provides a new child nasal decongesting device construction wherein the same can be utilized for relieving nasal congestion in children.

The general purpose of the present invention, which will be described subsequently in greater detail, is to provide a new child nasal decongesting device apparatus and method which has many of the advantages of the nasal decongesting devices mentioned heretofore and many novel features that result in a new child nasal decongesting device which is not anticipated, rendered obvious, suggested, or even implied by any of the prior art nasal decongesting devices, either alone or in any combination thereof.

To attain this, the present invention generally comprises a bulb defining an air cavity therein and a facemask outwardly extending from the bulb. The facemask has an open distal end opposite the bulb designed for positioning over a mouth and nostrils of a user such that the mouth and nostrils of the user are covered by the distal end of the facemask. An elongate tube outwardly extends from the bulb through the facemask. The tube is in fluid communication with the air cavity and has an open distal end outwardly extending from the distal end of the facemask and which is designed for insertion into the mouth of the user when the distal end of the facemask is positioned over the user's mouth and nostrils.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new child nasal decongesting device apparatus and method which has many of the advantages of the nasal decongesting devices mentioned heretofore and many novel features that result in a new child nasal decongesting device which is not anticipated, rendered obvious, suggested, or even implied by any of the prior art nasal decongesting devices, either alone or in any combination thereof.

It is another object of the present invention to provide a new child nasal decongesting device which may be easily and efficiently manufactured and marketed.

It is a further object of the present invention to provide a new child nasal decongesting device which is of a durable and reliable construction.

An even further object of the present invention is to provide a new child nasal decongesting device which is susceptible of a low cost of manufacture with regard to both materials and labor, and which accordingly is then susceptible of low prices of sale to the consuming public, thereby making such child nasal decongesting device economically available to the buying public.

Still yet another object of the present invention is to provide a new child nasal decongesting device which provides in the apparatuses and methods of the prior art some of the advantages thereof, while simultaneously overcoming some of the disadvantages normally associated therewith.

Still another object of the present invention is to provide a new child nasal decongesting device for relieving nasal congestion in children.

Yet another object of the present invention is to provide a new child nasal decongesting device which includes a bulb defining an air cavity therein and a facemask outwardly extending from the bulb. The facemask has an open distal end opposite the bulb designed for positioning over a mouth and nostrils of a user such that the mouth and nostrils of the user are covered by the distal end of the facemask. An elongate tube outwardly extends from the bulb through the facemask. The tube is in fluid communication with the air cavity and has an open distal end outwardly extending from the distal end of the facemask and which is designed for insertion into the mouth of the user when the distal end of the facemask is positioned over the user's mouth and nostrils.

Still yet another object of the present invention is to provide a new child nasal decongesting device that provides a means for blowing an infant's nose to clear the infant's nose of mucous fluids clogging the nasal passages.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
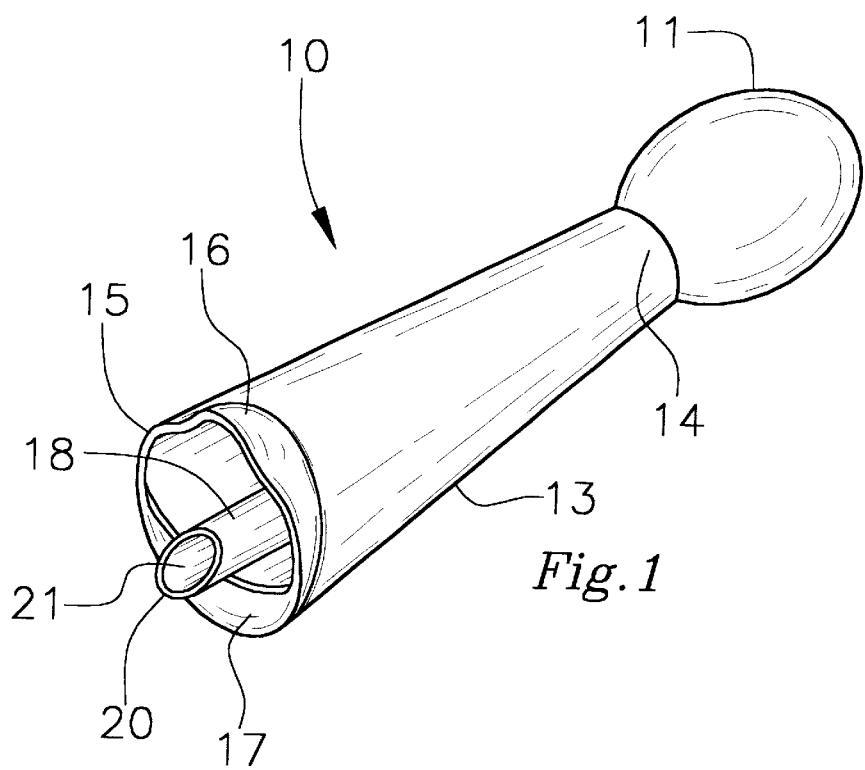
FIG. 1 is a schematic perspective view of a new child nasal decongesting device according to the present invention.
Figure 2:
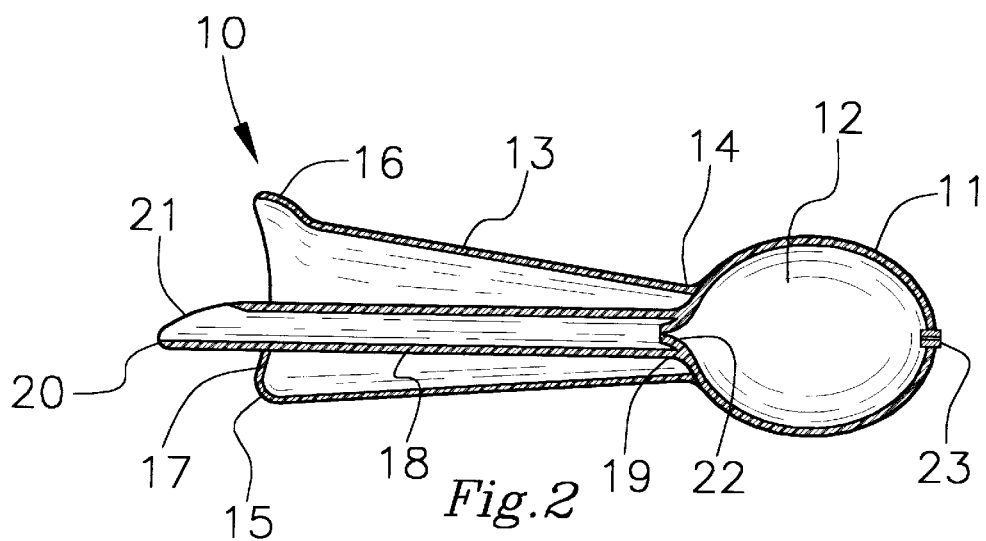
FIG. 2 is a schematic longitudinal cross sectional view of the present invention.
Figure 3:
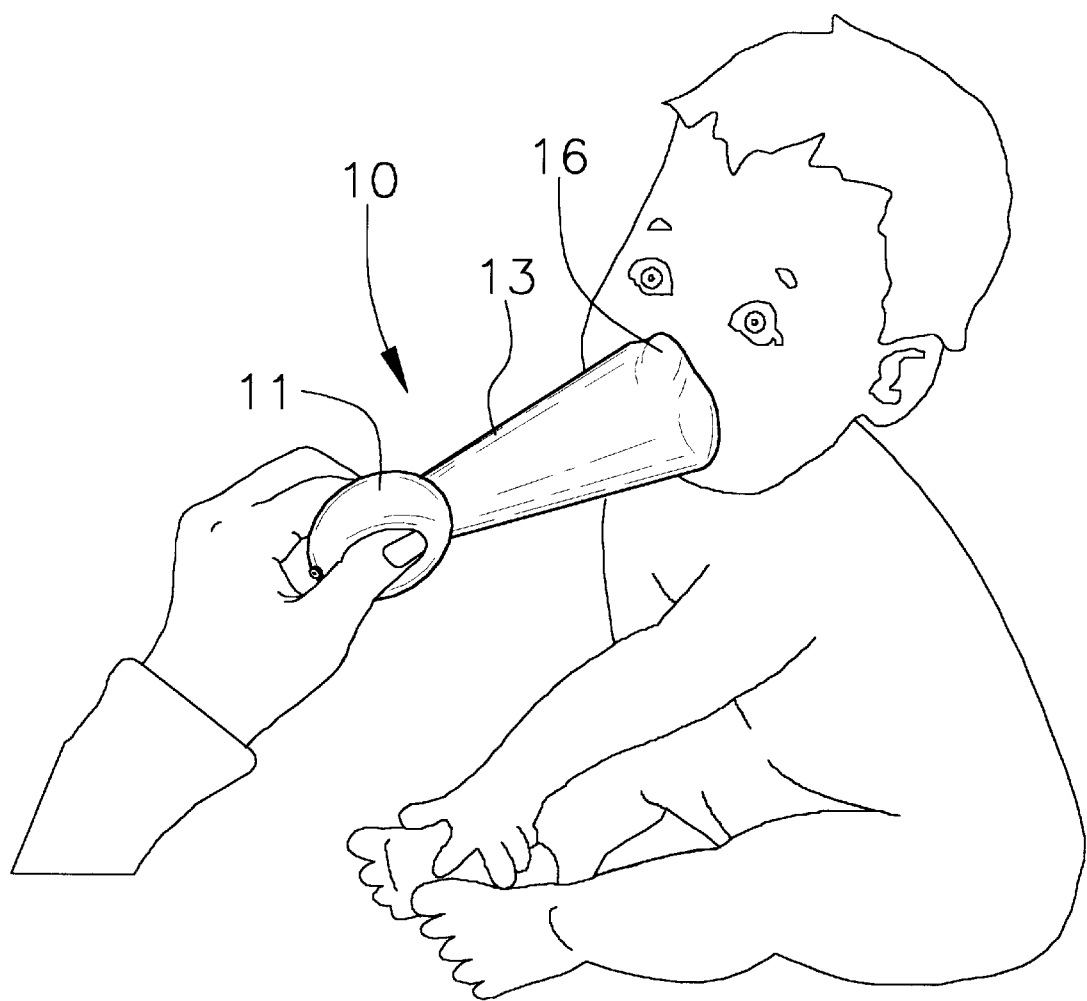
FIG. 3 is a schematic perspective view of the present invention in use.

With reference now to the drawings, and in particular to FIGS. 1 through 3 thereof, a new child nasal decongesting device embodying the principles and concepts of the present invention and generally designated by the reference numeral 10 will be described.

As best illustrated in FIGS. 1 through 3, the child nasal decongesting device 10 generally comprises a bulb defining an air cavity therein and a facemask outwardly extending from the bulb. The facemask has an open distal end opposite the bulb designed for positioning over a mouth and nostrils of a user such that the mouth and nostrils of the user are covered by the distal end of the facemask. An elongate tube outwardly extends from the bulb through the facemask. The tube is in fluid communication with the air cavity and has an open distal end outwardly extending from the distal end of the facemask and which is designed for insertion into the mouth of the user when the distal end of the facemask is positioned over the user's mouth and nostrils.

In closer detail, the nasal decongesting device 10 includes a generally ovaloid or egg-shaped resiliently deformable squeezable bulb 11 defining an air cavity therein 12. A preferably resiliently deformable generally frusta-conical tubular facemask 13 outwardly extends from the bulb. The facemask has a proximal end 14 and an open distal end 15 opposite the proximal end of the facemask. The proximal end of the face mast is coupled to the bulb. The facemask flares outwards from the proximal end of the facemask to the distal end of the facemask such that the distal end of the facemask has an outer diameter greater than that of the proximal end of the facemask.

In use, the distal end of the facemask is designed for positioning over a mouth and nostrils of a user such that the mouth and nostrils of the user are covered by the distal end of the facemask. Preferably, the distal end of the facemask has an outwardly flaring upper portion forming a nosepiece 16 designed for receiving therein a nose of the user when the distal end of the facemask is positioned over the user's mouth and nostrils. The distal end of the facemask also preferably has an inwardly extending lower portion forming a chin guard 17 designed for abutting a chin of the user when the distal end of the facemask is positioned over the user's mouth and nostrils.

An elongate tube 18 outwardly extends from the bulb through the facemask. The tube has opposite open proximal and distal ends 19,20 and a longitudinal axis extending between the proximal and distal ends of the tube. The proximal end of the tube is coupled to the bulb and is in fluid communication with the air cavity of the bulb. The distal end of the tube is outwardly extended from the distal end of the facemask. Preferably, a portion of the tube adjacent the distal end of the tube is coupled to the chin guard of the distal end of the facemask.

In use, the distal end of the tube is designed for insertion into the mouth of the user when the distal end of the facemask is positioned over the user's mouth and nostrils. The distal end of the tube has an opening 21 into the tube. In use, squeezing of the bulb forces air out of the air cavity through the tube and into the user's mouth. The forced air then flows into the user's nose and out the user's nostrils into the facemask via the distal end of the facemask. As the forced air flows out of the user's nose, it forces mucous nasal congestion out the user's nostrils and into the facemask where it is collected.

Preferably, as best illustrated in FIG. 2, the opening of the distal end of the tube has a generally oval periphery lying in a plane extending at an acute angle to the longitudinal axis of the tube for helping direct the forced air up from the user's mouth into the user's nasal passages.

In a preferred embodiment, the tube has a one-way valve 22 therein at the proximal end of the tube for permitting flow of air from the air cavity of the bulb into the tube while blocking flow of air in the tube back into the air cavity of the bulb. Also in this preferred embodiment, the bulb has an opening into the air cavity and a one-way valve 23 selectively closing the opening of the bulb for permitting flow of air into the air cavity via the opening of the bulb while blocking flow of air out of the air cavity via the opening of the bulb.

In an ideal embodiment, the nasal decongesting device has an overall length defined between the bulb and the distal end of the tube between about 3 inches and about 12 inches. Even more preferably, the overall length of the tube is between about 6 inches and about 10 inches. Also ideally, the nasal decongesting device has a maximum outer diameter defined at the distal end of the facemask between about 2 inches and about 4 inches.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A nasal decongesting device, comprising:
   a bulb defining an air cavity therein;
   a facemask outwardly extending from said bulb;
   said facemask having an open distal end opposite said bulb;
   said distal end of said facemask being adapted for positioning over a mouth and nostrils of a user such that the mouth and nostrils of the user are covered by said distal end of said facemask:
   an elongate tube outwardly extending from said bulb through said facemask;
   said tube being in fluid communication with said air cavity and having an open distal end outwardly extending from said distal end of said facemask, said distal end of said tube being adapted for insertion into the mouth of the user when said distal end of said facemask is positioned over the user's mouth and nostrils; and
   said distal end of said tube having an opening into said tube, said opening having a generally oval periphery lying, in a plane extending at an acute angle to a longitudinal axis of said tube for reducing the user's ability to block said opening with the user's tongue.

2. The nasal decongesting device of claim 1, said facemask flares outwards from said bulb to said distal end of said facemask such that said distal end of said facemask has an outer diameter greater than at a proximal end of said facemask adjacent said bulb.

3. The nasal decongesting device of claim 1, wherein said distal end of said facemask has an outwardly flaring upper portion forming a nosepiece portion of the facemask for receiving, therein a nose of the user when said distal end of said facemask is positioned over the user's mouth and nostrils such that the opening of said tube is oriented upwardly toward the nosepiece portion of said facemask for positioning said opening toward a top of the user's mouth for reducing the user's ability to block said opening with the user's tongue.

4. The nasal decongesting device of claim 1, wherein said distal end of said facemask has an inwardly extending lower portion forming a chin guard adapted for abutting a chin of the user when said distal end of said facemask is positioned over the user's mouth and nostrils, said chin Guard forming a well at the distal end of said facemask for blocking drainage of dislodged mucus from an interior of said facemask during use.

5. The nasal decongesting device of claim 4, wherein a portion of said tube adjacent said distal end of said tube is coupled to said chin guard of said distal end of said facemask.

6. The nasal decongesting device of claim 1, wherein said tube has a one-way valve therein for permitting flow of air from said air cavity of said bulb into said tube while blocking flow of air in said tube into said air cavity of said bulb.

7. The nasal decongesting device of claim 6, wherein said bulb has an opening into said air cavity and a one-way valve selectively closing said opening of said bulb for permitting flow of air into said air cavity via said opening of said bulb while blocking flow of air out of said air cavity via said opening of said bulb.

8. The nasal decongesting device of claim 1 wherein said facemask has a length and said tube has a length, and wherein the length of said facemask is approximately 80% of the length of said tube for reducing the chance for over insertion of said tube into the mouth of the user.

9. A nasal decongesting device, comprising:
   a resiliently deformable bulb defining an air cavity therein;
   a generally frusta-conical tubular facemask outwardly extending from said bulb;
   said facemask having a proximal end and an open distal end opposite said proximal end of said facemask, said proximal end of said facemask beings coupled to said bulb, said facemask flaring outwards from said proximal end of said facemask to said distal end of said facemask such that said distal end of said facemask has an outer diameter greater than that of said proximal end of said facemask;
   said distal end of said facemask being adapted for positioning over a mouth and nostrils of a user such that the mouth and nostrils of the user are covered by said distal end of said facemask;
   said distal end of said facemask having an outwardly flaring upper portion forming a nosepiece adapted for receiving therein a nose of the user when said distal end of said facemask is positioned over the user's mouth and nostrils;
   said distal end of said facemask having) an inwardly extending lower portion forming a chin guard adapted for abutting a chin of the user when said distal end of said facemask is positioned over the user's mouth and nostrils;
   an elongate tube outwardly extending from said bulb through said facemask;
   said tube having opposite proximal and distal ends and a longitudinal axis extending between said proximal and distal ends of said tube, said proximal end of said tube being coupled to said bulb and being in fluid communication with said air cavity of said bulb;
   said distal end of said tube being, outwardly extended from said distal end of said facemask a portion of said tube adjacent said distal end of said tube being coupled to said chin guard of said distal end of said facemask;
   said distal end of said tube being adapted for insertion into the mouth of the user when said distal end of said facemask is positioned over the user s mouth and nostrils;

said distal end of said tube having an opening into said tube, said opening having a periphery lying in a plane extending at an acute angle to said longitudinal axis of said tube;

said tube having a one-way valve therein at said proximal end of said tube for permitting flow of air from said air cavity of said bulb into said tube while blocking flow of air in said tube into said air cavity of said bulb; and said bulb having an opening into said air cavity and a one-way valve selectively closing said opening of said bulb for permitting flow of air into said air cavity via said opening of said bulb while blocking flow of air out of said air cavity via said opening of said bulb.

\* \* \* \* \*